United States Patent [19]

Takeda et al.

[11] Patent Number: 5,707,838
[45] Date of Patent: Jan. 13, 1998

[54] ANTIBIOTIC PRODUCED BY PSEUDOMONAS SP. AND PROCESS FOR THE PREPARATION THEREOF

[75] Inventors: Reiji Takeda, Kobe; Shigetada Hidaka; Shinobu Kobayashi, both of Shiga; Yoshio Hayase, Kameyama; Mamoru Ozaki, Kusatsu; Hiroshi Nakai, Nara, all of Japan

[73] Assignee: Shionogi & Co., Ltd., Osaka, Japan

[21] Appl. No.: 619,508

[22] PCT Filed: Aug. 4, 1995

[86] PCT No.: PCT/JP95/01552

§ 371 Date: Mar. 28, 1996

§ 102(e) Date: Mar. 28, 1996

[87] PCT Pub. No.: WO96/04262

PCT Pub. Date: Feb. 15, 1996

[30] Foreign Application Priority Data

Aug. 5, 1994 [JP] Japan ................................ 6-184489

[51] Int. Cl.$^6$ .................... C12P 17/16; A61K 31/38; A61K 31/425; C07D 277/56
[52] U.S. Cl. .................... 435/118; 514/443; 548/101; 548/104; 548/105; 548/148
[58] Field of Search ........................ 435/118, 170, 435/874; 548/104, 106, 108, 109, 101, 105, 148; 514/443

[56] References Cited

U.S. PATENT DOCUMENTS 4,406,905 9/1983 Zahner et al. ..................... 514/342

FOREIGN PATENT DOCUMENTS 0 045 281 2/1982 Germany .
57-58682 4/1982 Japan .
64-22861 1/1989 Japan .

OTHER PUBLICATIONS

Cox et al., Pyochelin: Novel structure of an iron-chelating growth promoter for *Pseudomonas aeruginosa*, Proc. Natl. Acad. Sci. USA, vol. 7, pp. 4256–4260, 1981.

Krieg, ed., Section 4. Gram–negative rods and cocci, In Bergey's Manual of Systematic Bacteriology, vol. 1, Williams and Wilkins, MD p. 165, 1984.

*Primary Examiner*—Irene Marx
*Assistant Examiner*—Janet M. Kerr
*Attorney, Agent, or Firm*—Foley & Lardner

[57] ABSTRACT

The invention is a compound of the formula:

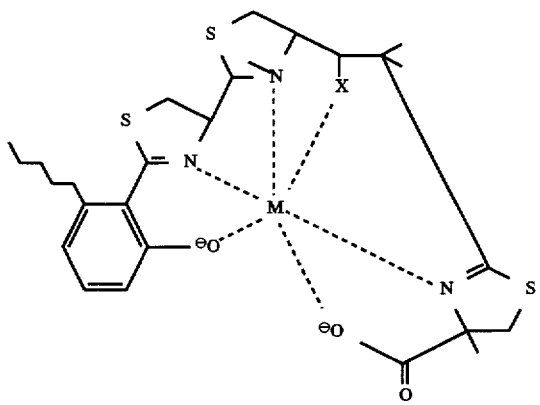

wherein M is a bivalent or trivalent metal ion, and X is OH or $O^{\ominus}$. The above compound of the present invention is useful for prevention or treatment of mycoplasmosis.

11 Claims, 10 Drawing Sheets

ANTIBIOTIC PRODUCED BY PSEUDOMONAS SP. AND PROCESS FOR THE PREPARATION THEREOF

DETAILED DESCRIPTION OF THE INVENTION

1. Field of the Invention

The present invention relates to a novel useful compound in the field of medicine and veterinary medicine, a process for preparation thereof and a pharmaceutical composition containing said compound.

2. Background of the Invention

Mycoplasmas have a wide distribution throughout domestic animals such as swine, cattle and sheep; domestic fowls such as chickens, turkeys and pheasant; insects; and plants, as well as human, and there exist many species of Mycoplasma for each of those animals.

For human, Mycoplasmas have attracted the attention of people as causative bacteria of pneumonia and upper respiratory inflammation, and recently, relation between infections of Mycoplasmas and other diseases, especially AIDS, is taken notice of people.

The bacteria cause various diseases such as epidemic pneumonia in swine, respiratory mycoplasmosis and infectious synovitis in chickens, and airsacculitis and infectious sinusitis in turkeys. These diseases are not caused only by Mycoplasma alone but can be accompanied by complications caused by infectious other microorganisms such as bacteria and viruses, which lead to a serious economic loss because, in such cases, the symptoms are severer and the diseases are chronic compared to those of infections with Mycoplasma alone.

Mycoplasmas also play an important role in infections of laboratory animals such as mice, rats and guinea pigs, and in contamination of tissue culture cells, which are all used for various studies, as well as infections of domestic animals and fowls.

OBJECT OF THE INVENTION

To prevent the infections and contaminations with Mycoplasma, macrolides and tetracyclines are often used because Mycoplasma is characterized by lacking the cell wall in its structure.

However, macrolides have been used for many years, and such long-term usage has led to developing many macrolides-resistant Mycoplasma strains, and the efficacy of tetracyclines is as well declining.

DESCRIPTION OF THE INVENTION

The present inventors have found a new substance produced by *Pseudomonas sp.*, and demonstrated that said substance had an anti-infection activity to Mycoplasma. Therefore, the new substance of the invention is considered to be very promising agent for prevention and/or treatment of Mycoplasmosis.

A compound of the present invention is represented by the formula:

wherein M is a bivalent or trivalent metal ion, and X is OH or $O^{\ominus}$.

The compound of the invention can be stereochemically represented by the formula:

wherein each symbol is as defined above.

Bivalent or trivalent metal ions represented by M include $Zn^{2+}$, $Cu^{2+}$, $Fe^{2+}$, $Fe^{3+}$, $Co^{2+}$, $Ni^{2+}$, $Mn^{2+}$, $Cd^{2+}$, $Mg^{2+}$, $Ca^{2+}$, $Sr^{2+}$, $Ba^{2+}$, $V^{2+}$, $V^{3+}$, $Cr^{2+}$, $Al^{3+}$, $Sn^{2+}$, $Pb^{2+}$, $Ag^{2+}$ or the like. Preferably, M is $Zn^{2+}$, $Cu^{2+}$, $Fe^{2+}$, $Fe^{3+}$, $Co^{2+}$, $Ni^{2+}$, $Mn^{2+}$, $Mn^{3+}$ and $Cd^{2+}$, and more preferably, $Zn^{2+}$, $Cu^{2+}$, $Fe^{3+}$, $Co^{2+}$ and $Ni^{2+}$.

Figure 1:
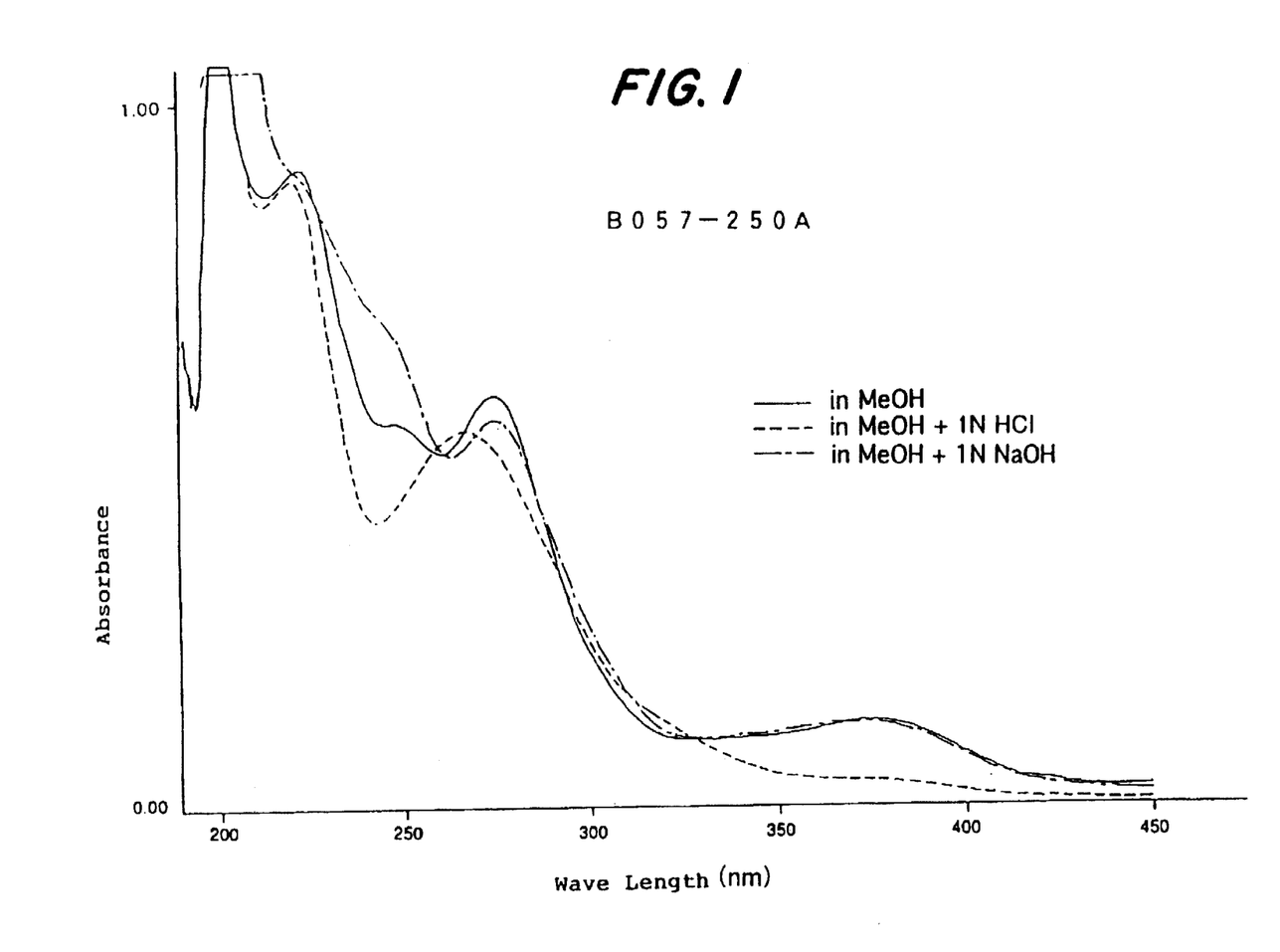
FIG. 1 shows UV absorption spectrum of B057-250A.
Figure 2:
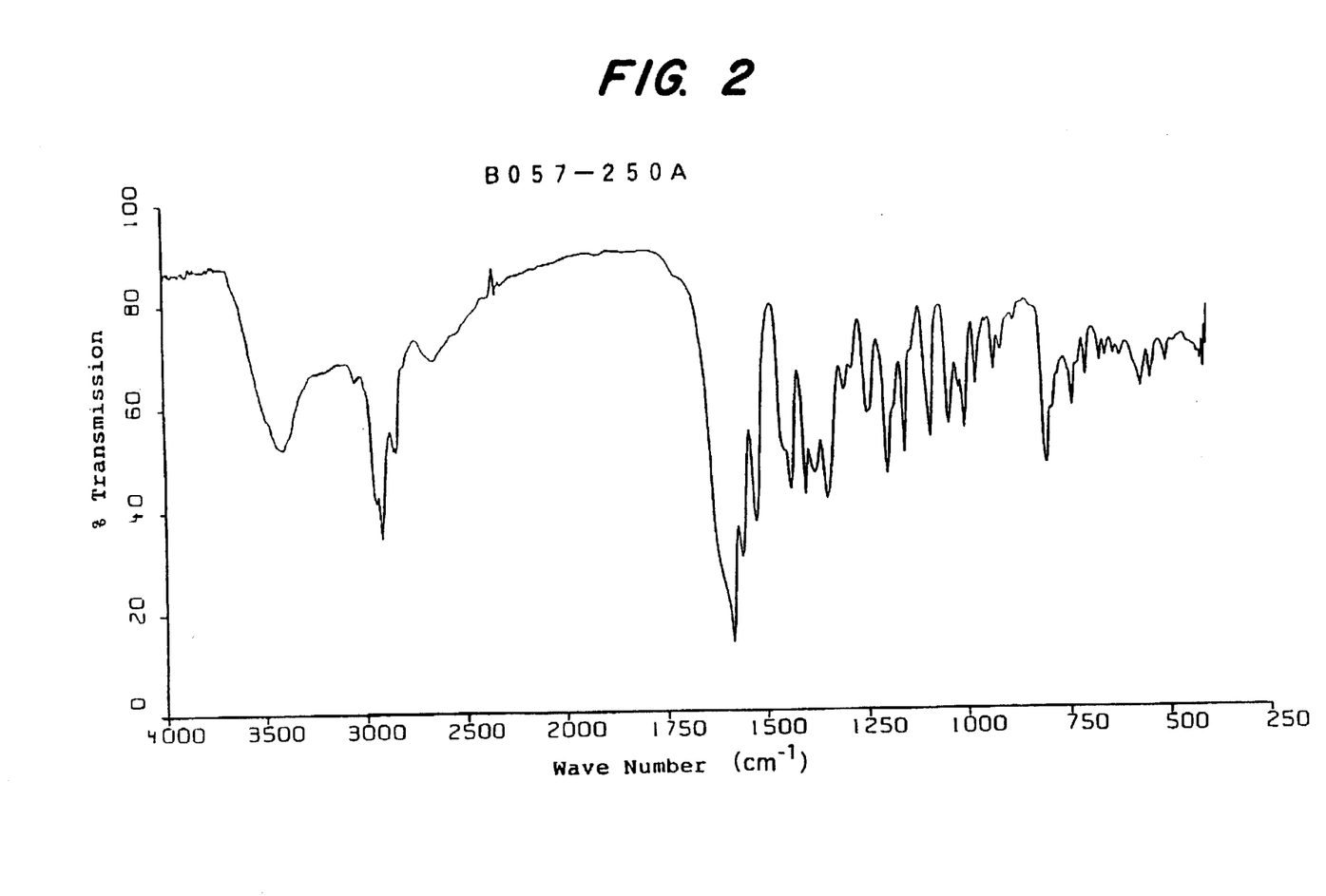
FIG. 2 shows infrared absorption spectrum of B057-250A.

A compound wherein M is $Cu^{2+}$, $Zn^{2+}$, $Fe^{3+}$, $Co^{2+}$ or $Ni^{2+}$ is herein referred to as B057-250A (Cu-chelate), B057-250B (Zn-chelate), B057-250C (Fe-chelate), B057-250D (Co-chelate) or B057-250E (Ni-chelate), respectively. They are collectively referred to as compounds B057-250. Physical and chemical characteristics of the new compound B057-250 are as follows:

1) B057-250A (Cu-chelate)
   Molecular formula: $C_{27}H_{37}N_3O_4S_3Cu$
   Mass spectrum (SIMS): m/z 627 (M+H)+
   Crystal/color: green needle-shaped crystal UV-absorption spectra: see FIG. 1
  UVλMeOH$_{max}$ (nm): 223, 275, 375
  UVλMeOH+NaOH$_{max}$ (nm): 275, 375
  UVλMeOH+HCl$_{max}$ (nm): 221,265
IRυKBr$_{max}$ cm$^{-1}$; 3414, 2926, 2666, 1589 cm$^{-1}$ (see FIG. 2)
Optical rotation: [α]$^{23}_D$ −1369.2±136° (c 0.104%, MeOH)
Solubility: soluble in methanol, ethanol, dichloromethane and chloroform; and insoluble in water, acetone, ethyl acetate, n-hexane and benzene.
Color reaction: positive to iodine and KMnO$_4$.
Thin layer chromatography: Rf value is 0.34 (see Note 1 below for the conditions).
High performance liquid chromatography: retention time is 11.6 minutes (see Note 2 below for the conditions).

Figure 3:
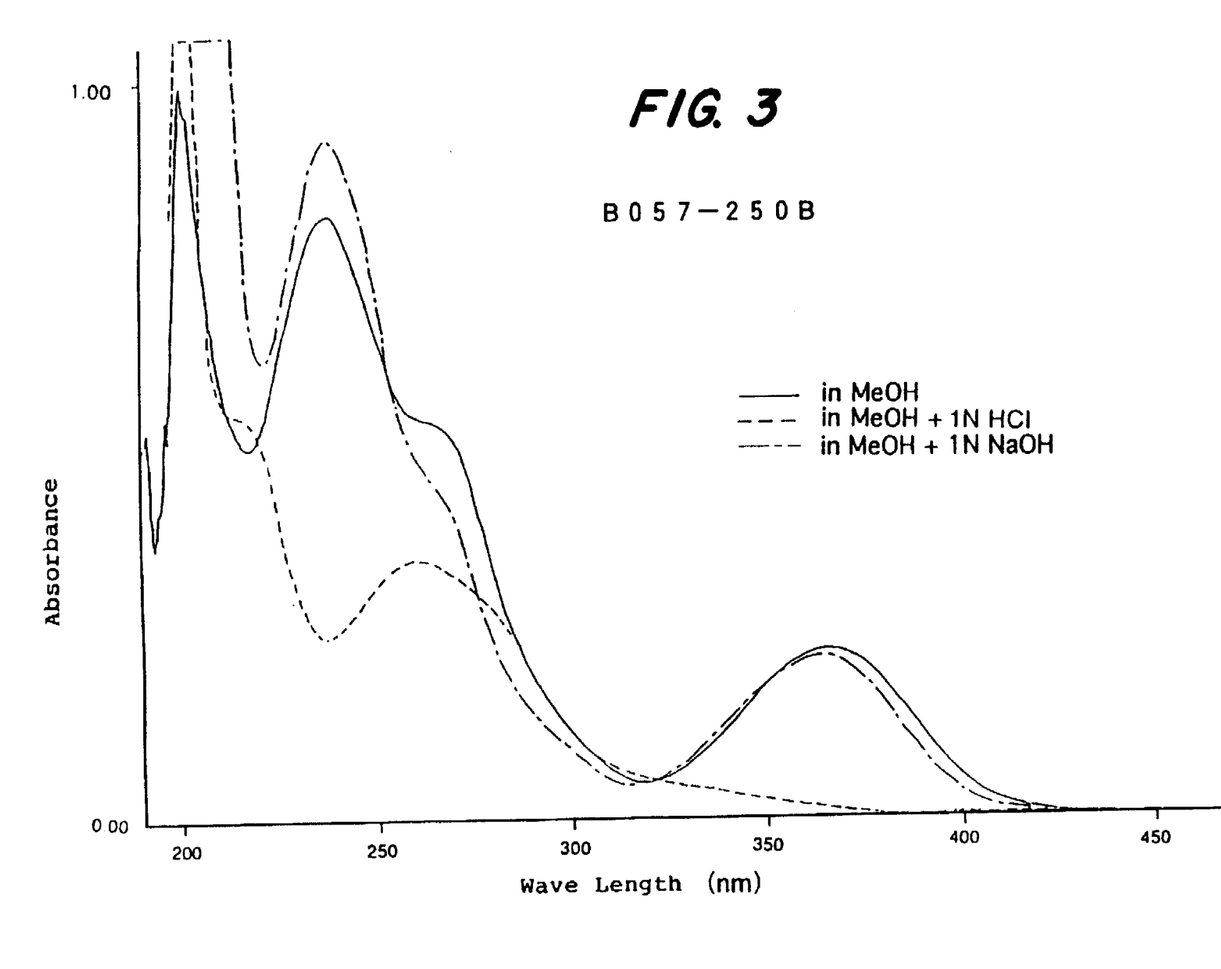
FIG. 3 shows UV absorption spectrum of B057-250B.
Figure 4:
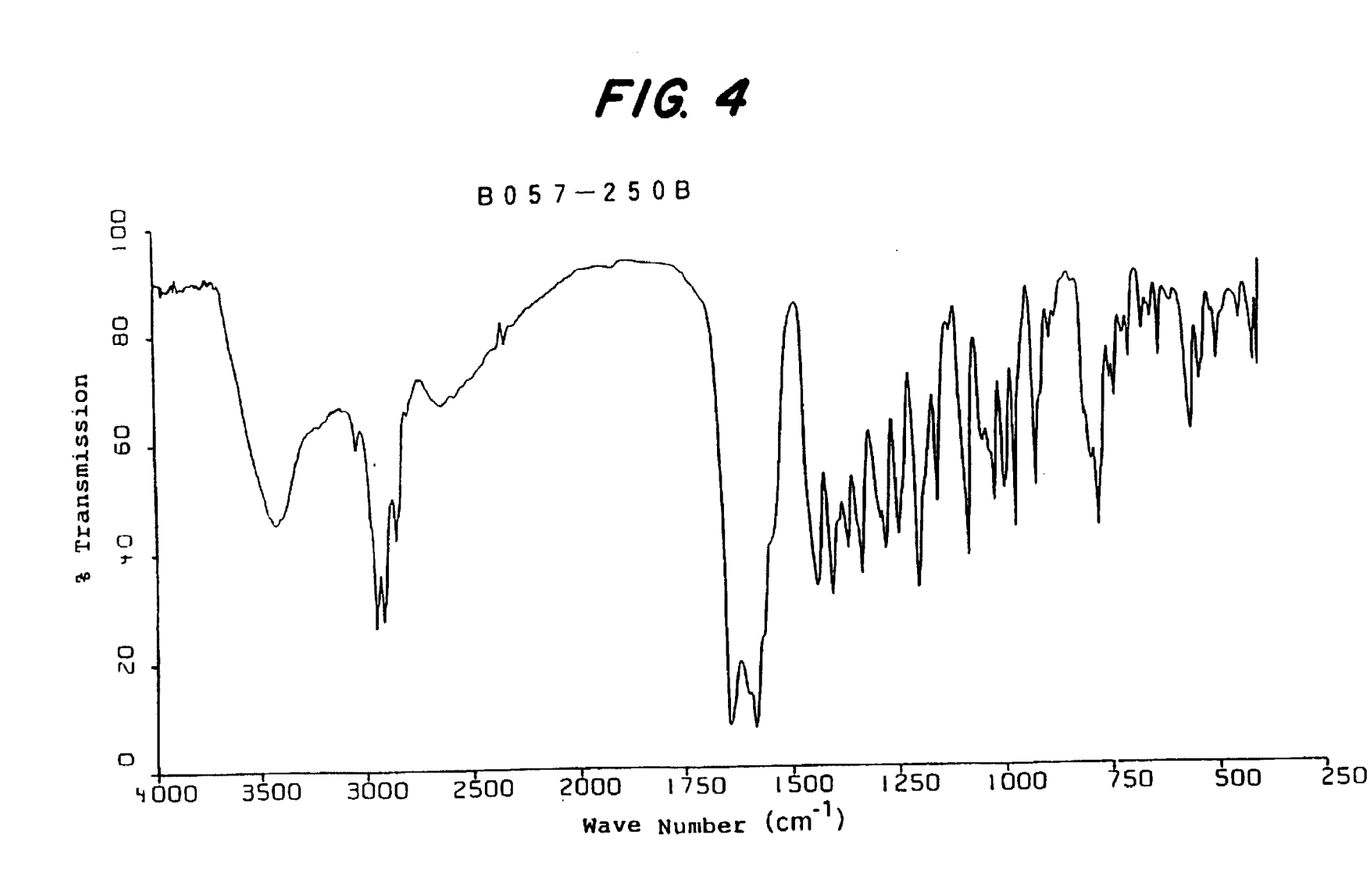
FIG. 4 shows infrared absorption spectrum of B057-250B.

B057-250B (Zn-chelate)
Molecular formula: $C_{27}H_{37}N_3O_4S_3Zn$ (determined by X-ray structure analysis)
Mass spectrum (SIMS): m/z 628 (M+H)+
m.p.: 226°–228 C° (decomposition)
Crystal/color: colourless, rhombic, board-shaped crystal
UV-absorption spectrum: see FIG. 3
  UVλMeOH$_{max}$ nm (ε): 238 nm (ε=19,900), 264 nm (shoulder, ε=12,900), 366 nm (ε=5,530)
  UVλMeOH+NaOH$_{max}$ (nm): 275, 375 nm
  UVλMeOH+HCl$_{max}$ nm: 221,265 nm
IRυKBr$_{max}$ cm$^{-1}$; 3430, 2963, 2658, 1648, 1590 cm$^{-1}$ (see FIG. 4)
$^1$H-NMR spectra and $^{13}$C-NMR spectra: the assignments are shown in Table 1 and in chemical formula below.
Optical rotation: [α]24$_D$ +53.2+0.9° (c: 0.990%, MeOH)
$^1$H and $^{13}$C NMR chemical shifts of B057-250-B (in CDCl$_3$ (7.5 mg/0.6 ml), 20° C.)

TABLE 1

| No. | δ $^{13}$C/ppm (m, $^1$J$_{C,H}$) | δ $^1$H/ppm (m, J) |
|---|---|---|
| 1 | 167.98 (s) | — |
| 2 | 121.44 (d, 157.8) | 6.657 (d, 7.38) |
| 3 | 132.94 (d, 157.7) | 7.040 (t, 7.47) |
| 4 | 120.21 (d, ~160) | 6.506 (d, 6.41) |
| 5 | 146.27 (s) | — |
| 5a | 35.71 (t, 126.8) | 2.725 (m), 3.139 (t-like, 11.11) |
| 5b | 33.62 (t. 126.2) | ~1.64 (m), ~1.58 (m) |
| 5c | 22.63 (t, 127.0) | ~1.43 (m) |
| 5d | 31.96 (t, 123.1) | ~1.40 (m) |
| 5e | 14.18 (q, 124.8) | 0.935 (t, 6.94) |
| 6 | 119.65 (s) | — |
| 7 | 172.74 (s) | — |
| 8 | 35.48 (t, 146.2) | 2.870 (t, 12.02), 3.502 (t, 9.05) |
| 9 | 75.11 (d, 144.8) | 4.469 (td, 10.82, 8.62) |
| 10 | 81.31 (d, 151.0) | 3.940 (d, 10.39) |
| 11 | 38.19 (t, 147.0) | 2.188 (t, 10.80), 2.639 (t-like, 8.86) |
| 12 | 72.35 (d, 136.5) | 3.068 (t, 7.56) |
| 13 | 48.16 (q, 139.9) | 2.351 (s) |
| 14 | ~77.2 (maybe d) | 3.607 (d, 5.67) |
| 14-OH | — | 10.293 (br) |
| 15 | 44.92 (s) | — |
| 15a | 29.04 (q, 129.7) | 1.617 (s) |
| 15b | 25.41 (q, 128.8) | 1.260 (s) |
| 16 | 182.37 (s) | — |
| 17 | 38.19 (t, 147.0) | 3.196 (d, 11.96), 3.763 (d, 11.96) |
| 18 | 86.04 (s) | — |
| 19 | 24.27 (q, 128.8) | 1.601 (s) |
| 20 | 177.12 (s) | — |

Solubility: soluble in methanol, ethanol, dichloromethane and chloroform; insoluble in water, acetone, ethyl acetate, n-hexane and benzene.
Color reaction: positive to iodine and KMnO$_4$; negative or ninhydrin reaction.
Thin layer chromatography: Rf value is 0.47 (see Note 1 below for the conditions).
High performance liquid chromatography: retention time is 14.2 minutes (see Note 2 below for the conditions).

Figure 5:
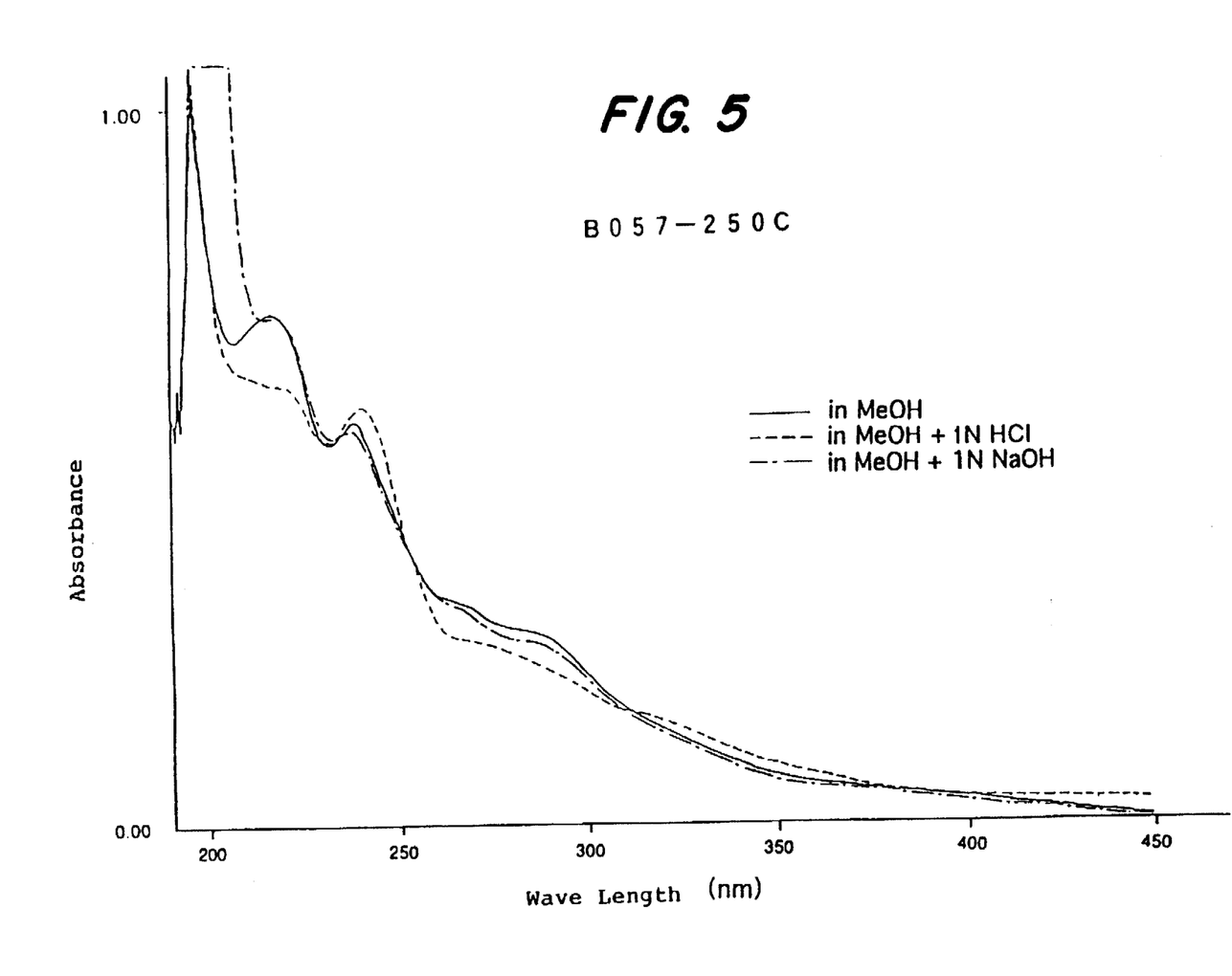
FIG. 5 shows UV absorption spectrum of B057-250C.
Figure 6:
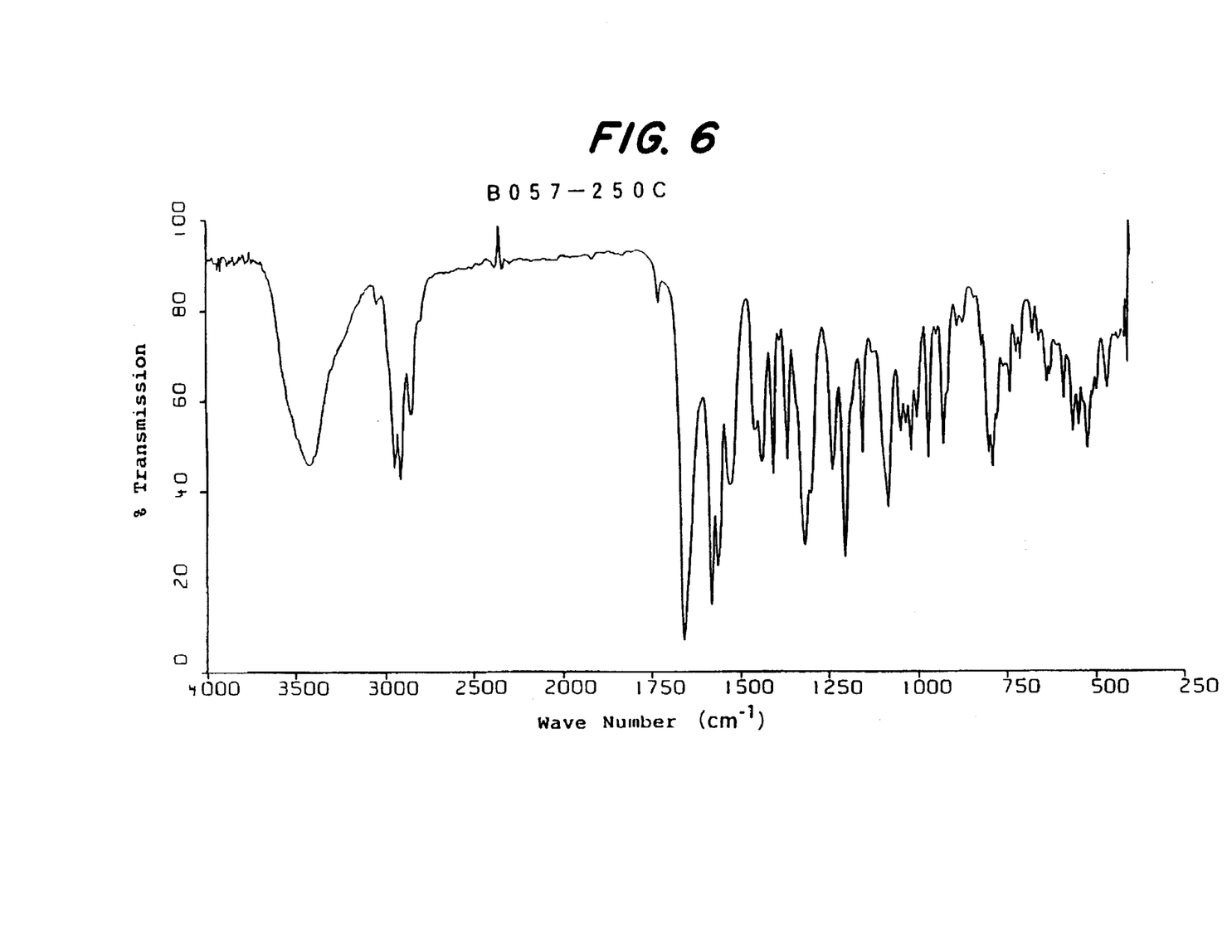
FIG. 6 shows infrared absorption spectrum of B057-250C.

3) B057-250C (Fe-chelate)
  Molecular formula: $C_{27}H_{36}N_3O_4S_3Fe$
  Mass spectrum (SIMS): m/z 619 (M+H)+
  Structure:

Color: reddish brown oil (not crystallized)
UV-absorption spectra: see FIG. 5
  UVλMeOH$_{max}$ (nm): 218, 239 nm
  UVλMeOH+NaOH$_{max}$ (nm): 219, 239 nm
  UVλMeOH+HCl$_{max}$ (nm): 221,242 nm
IRυKBr$_{max}$ cm$^{-1}$; 3433, 2927, 1664 cm$^{-1}$ (see FIG. 6)
Solubility: soluble in methanol, ethanol, dichloromethane and chloroform; insoluble in water, acetone, ethyl acetate, n-hexane and benzene.
Color reaction: positive to iodine and $KMnO_4$.
Thin layer chromatography: Rf value is 0.65 (see Note 1 below for the conditions).
High performance liquid chromatography: retention time is 15.7 minutes (see Note 2 below for the conditions).

Note 1) Conditions for thin layer chromatography
  Thin layer plate: Silica-gel 60 $F_{254}$ (Merck, No. 5715)
  Carrier solvent: chloroform: methanol (9:1, v/v)
Note 2) High performance liquid chromatography
  Column: STR-ODS$_M$, ID4.6 mm×250 mm, Shimadzu Techno Research
  Mobile phase: methanol:water (7:3, v/v)
  Detection: UV 235 nm
  Temperature: 40° C.

Figure 7:
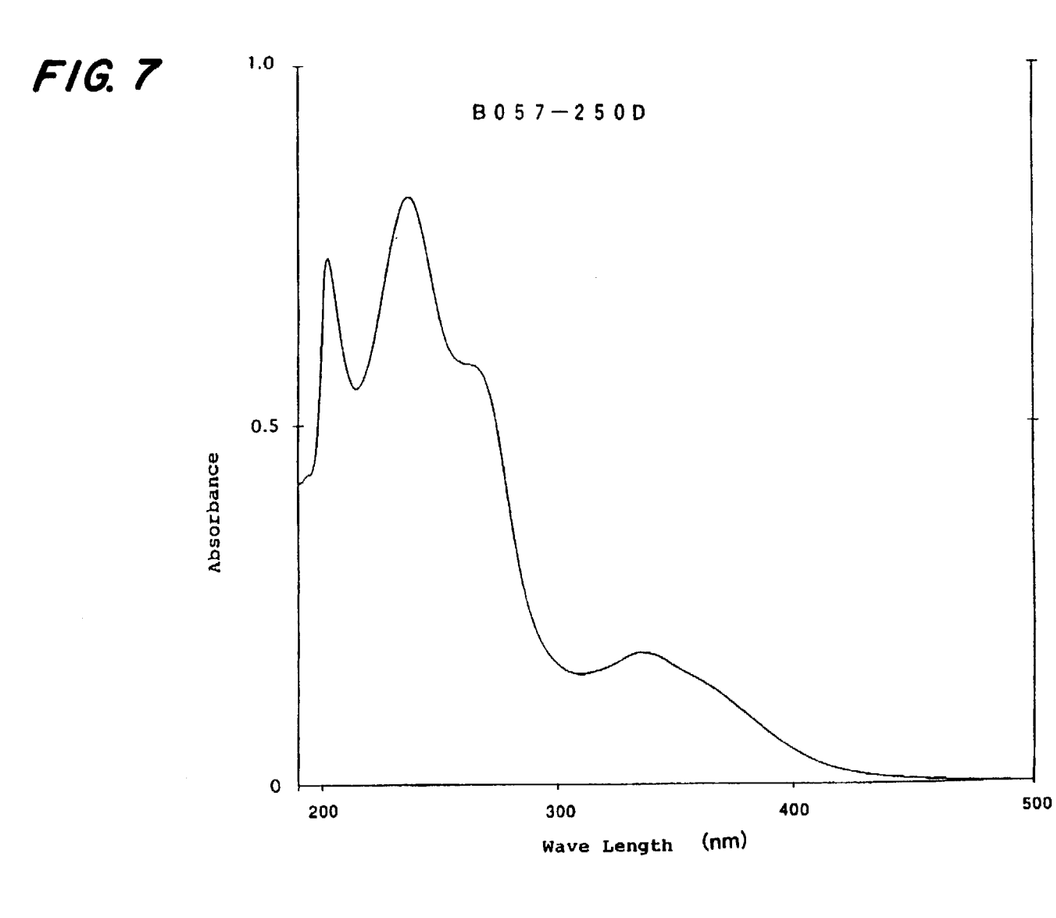
FIG. 7 shows UV absorption spectrum of B057-250D.
Figure 8:
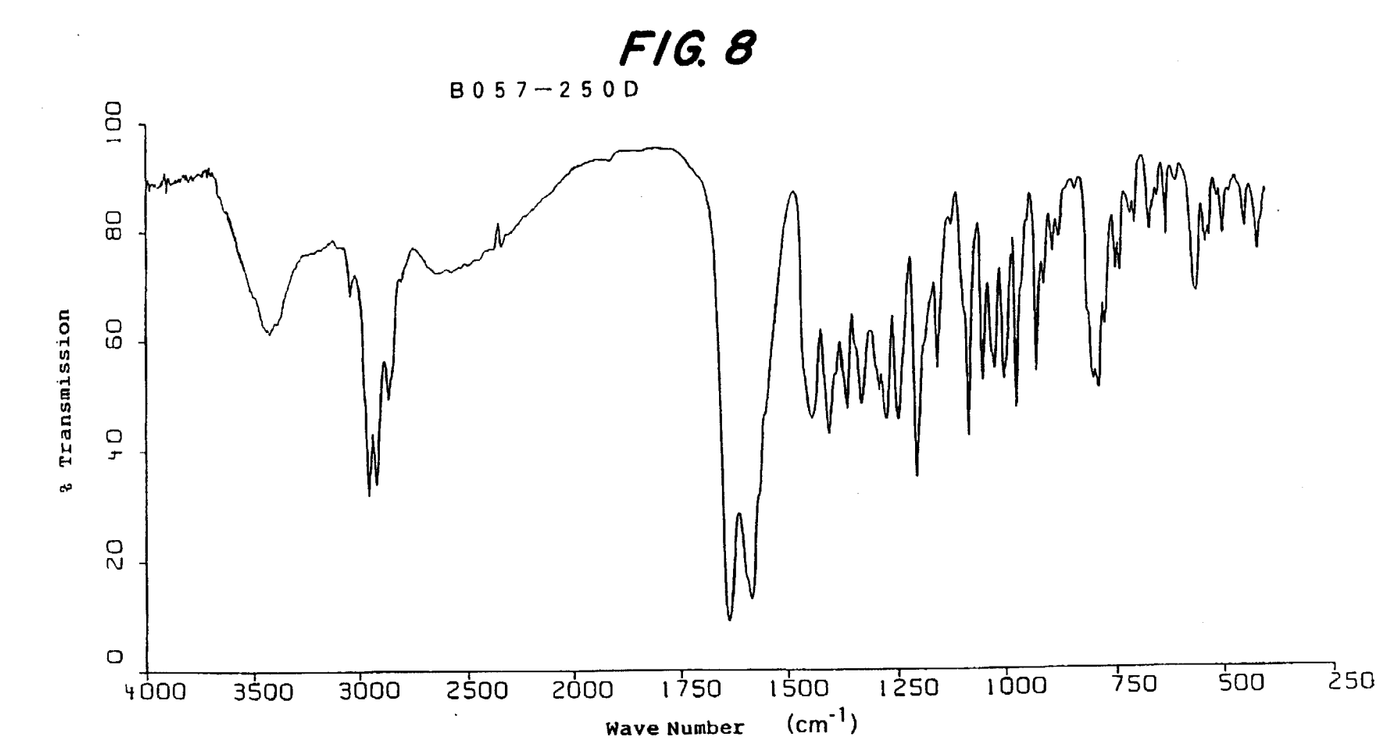
FIG. 8 shows infrared absorption spectrum of B057-250D.

4) B057-250D (Co-chelate)
  Appearance: brown granular crystal
  m.p.(° C.): 251–253
  Molecular formula: $C_{27}H_{37}N_3O_4S_3Co$
  Mass spectrum (SIMS): m/z 623 (M+H)+
  UVυMeOH$_{max}$ nm (ε): 202 (22,800), 237 (25,500), 265 (18,300), 337 (5,600) (see FIG. 7)
  IRυKBr$_{max}$ cm$^{-1}$; 2962, 2926, 2813, 1642, 1589, 1446, 1408, 1209, 1088, 802 (see FIG. 8)
  Optical rotation: $[\alpha]^{23}_D$+28.4±0.7° (c: 0.95, MeOH)
  Solubility: soluble in methanol and chloroform: insoluble in water.

Figure 9:
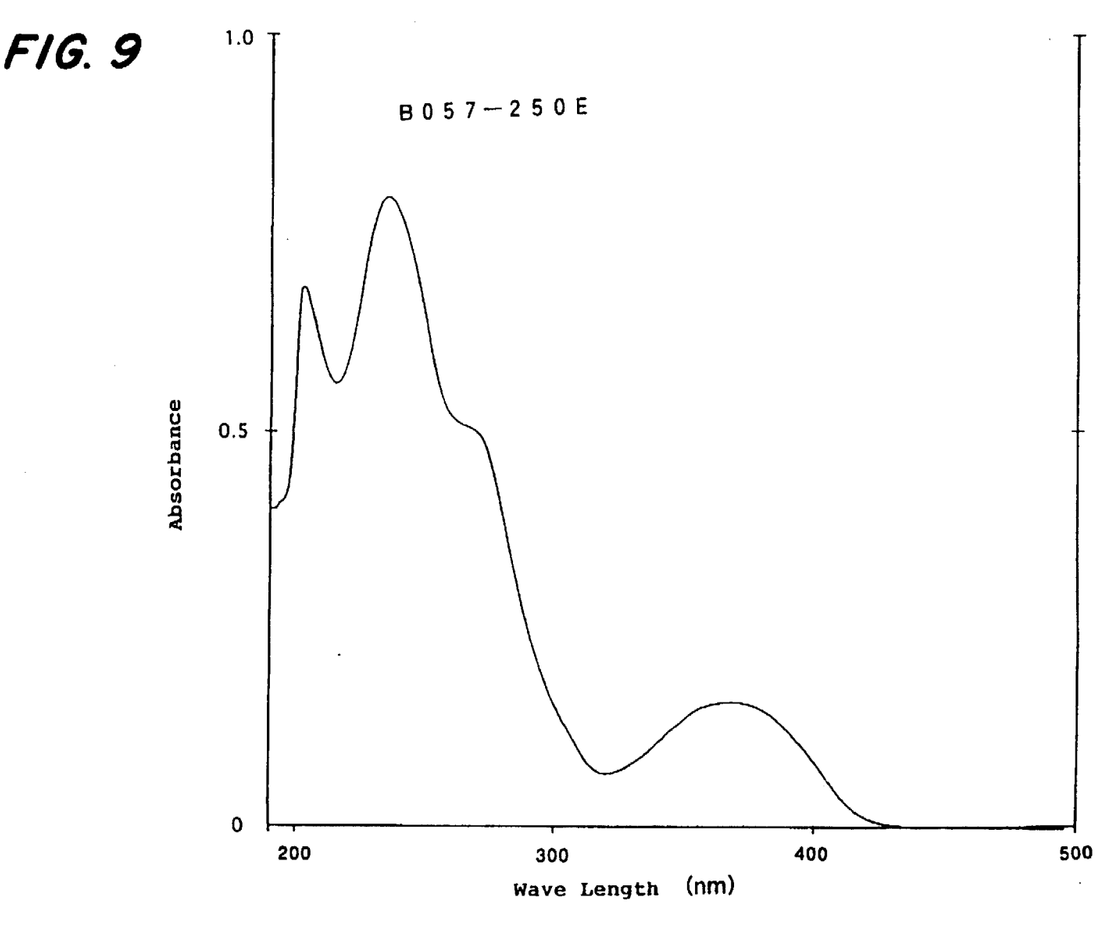
FIG. 9 shows UV absorption spectrum of B057-250E.
Figure 10:
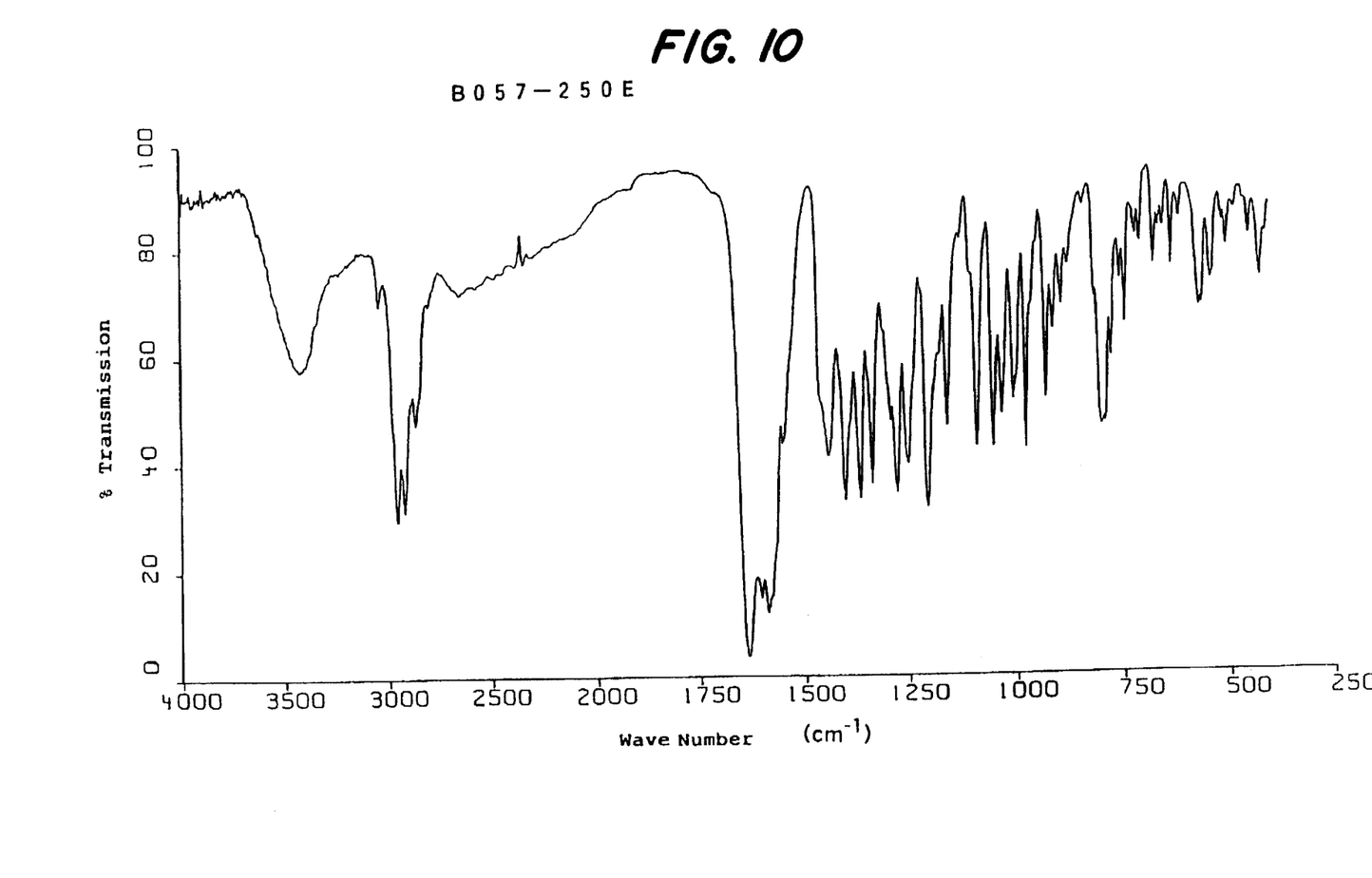
FIG. 10 shows infrared absorption spectrum of B057-250E.

5) B057-250E (Ni-chelate)
  Appearance: green rhombic, board-shaped crystal
  M.p. (° C.): 287–288
  Molecular formula: $C_{27}H_{37}N_3O_4S_3Ni$
  Mass spectrum (SIMS): m/z 622 (M+H)+
  UVλMeOH$_{max}$ nm (ε): 202 (21,300), 235 (24,800), 265 (15,600), 370 (4,700) (see FIG. 9)
  IRυKBr$_{max}$ cm$^{-1}$; 2960, 2925, 2871, 1639, 1593, 1445, 1405, 1206, 1091, 800 (see FIG. 10)
  Optical rotation: $[\alpha]^{23}_D$+197.6±4.9° (c: 0.49, MeOH)
  Solubility: soluble in methanol and chloroform; insoluble in water.

Compound B057-250of the present invention is prepared by cultivating a microorganism which belongs to Pseudomonas and produces a compound of the formula:

wherein M° is $Cu^{2+}$, $Zn^{2+}$ or $Fe^{3+}$, and X is OH or O, such as Pseudomonas sp. No. 57-250, extracting and collecting the compound from the culture, followed by optionally reacting said compound in a state of a solution with a solution containing a bivalent or trivalent metal ion.

The present invention further relates to Pseudomonas sp. No. 57-250. The name of this strain is herein abbreviated as "strain No. 57-250". The characteristics of the strain is as follows:

1. Morphology:
  It is a Gram-negative rod, and 0.5–0.6 μm×2.0–3.0 μm in size.
  It has motility with one or more polar flagella.
2. Findings in Culture:
  1) Culture in broth medium
    A bit slow growth of bacteria, observed a slight yellowish white precipitate.
  2) Stab culture in broth agar
    Observed growth in thread form along the stab line with broad growth appearing on the surface of the medium.
    No production of gas and pigment was observed.
  3) Slant culture in broth agar
    A bit of slow growth of bacteria was observed. The bacterial cells were yellowish white, dull glossy and wet. Flat swelling was observed. Transparency: translucent in an early stage of culture, and then turned to opaque with the lapse of time. No production of gas and pigment was observed.
  4) Cultivation on broth agar plate medium:
    A bit of slow growth of bacteria was observed. Colony: translucent and yellowish-white small dot and thereafter growing into opaque and yellowish-white round form with flat or round swelling. No production of gas and soluble pigment was observed.
3. Physiological and Biochemical Properties
  (1) Requirement of oxygen: Yes
  (2) Optimal temperature for growth: 30° C. (well growing at 28° C. and 37° C., slow growing at 10° C., and not growing at 4° C. and 41° C.)
  (3) Optimal. pH for growth: pH 7 ( grew at pH 5–8, but did not grow at pH 4 and pH 9)
  (4) Denitrification: negative
  (5) Reduction of nitrate: negative
  (6) Oxidase test: positive
  (7) Urease test: positive (8) Catalase test: positive (weakly)

(9) Liquefaction of gelatin: negative (10) Starch degradation: negative (11) Methyl red test: negative (12) V-P test: negative (13) Production of indole: negative (14) Production of $H_2S$: negative (15) Availability of citric acid: positive (Christensen medium and Simons medium)

(16) Hydrolizing ability for Tween 80 (polyoxyethylene sorbitan monolate): positive (slow)

(17) Hydrolizing ability for escrine: negative (18) Hydrolizing ability for arginine: negative (19) Decarboxylation of lysin: negative (20) Decarboxylation of ornithine: negative (21) β-galactosidase: negative (22) Coagulation of milk: negative (23) Peptonization of milk: negative (24) O-F test: oxidized (slow)

(25) Accumulation of PHB: negative (26) Quinone type: Q8

(27) Fluorescent pigment: negative (28) Acid-producing ability from sugar:

An acid is produced from D-glucose, D-galactose and D-xylose, and not produced from D-fructose, maltose, D-mannitol, lactose, sucrose, D-arabinose, D-sorbitol, D-mannose and D-trehalose.

(29) Assimilating ability of carbon sources

It can assimilate as a single carbon source D-glucose, D-galactose, D-xylose, inositol succinate and lactic acid to form the bacterial cells thereof.

On the other hand, it did not assimilate D-fructose, maltose, D-mannitol, lactose, sucrose, D-arabinose, D-sorbitol, D-mannose and D-trehalose, geraniol, L-valine, β-alanine, DL-arginine, betaine and methanol.

The growth of strain No. 57-250 in an inorganic salt medium containing a sole carbon source is very slow and weak.

The bacterium is a gram-negative rod, and moves using one or more polar flagella. It is slightly catalase positive and has an oxidase. O-F test showed weak oxidation.

In view of these results, the present bacteria are considered to belong to Pseudomonas. Therefore, their properties were further compared with those of Pseudomonas species described in Bergey's Manual of Systematic Bacteriology Vol.1, and it can be found that no species have properties consistent or analogous to those of the present bacteria. Thus, the bacteria was designated as *Pseudomonas sp.* No.57-250.

The strain was deposited under accession No. FERM P-14235 with National Institute of Bioscience and Human Technology, Higashi 1-1-3, Tsukuba, Ibaraki, JAPAN on Mar. 17, 1994 and then transferred to the International Deposition under Budapest Treaty on Jun. 22, 1995, and assigned to accession No. FERM BP-5143.

GENERAL DESCRIPTION

A general procedure for preparing compound B057-250of the present invention will be described below.

1) Cultivation Method

Cultivation of *Pseudomonas sp.* No. 57-250 can be performed in various liquid media having different compositions. A medium useful for producing compound B057-250 (Cu-, Zn- and Fe-chelates) contains carbon sources such as glucose and nitrogen sources such as yeast extract, soy bean powder and pharmamedia. If necessary, metal salts such as calcium carbonate, Zn, Cu and Fe salts are also used in preparing the medium. Anti-foaming agents such as polyethyleneglycol may be added if necessary. The cultivation is usually performed aerobically, and aeration-agitation culture is preferred. The cultivation temperature may be suitably changed as far as the bacteria are allowed to grow for production of compound B057-250(Cu-, Zn- and Fe-chelates), however, the preferred temperature is 23°–28° C. A preferable pH is around 7, and the cultivation is usually performed for about 24–48 hours and terminated at a proper time when the titer of the compound B057-250(Cu-, Zn- and Fe-chelates) reaches maximum.

2) Extracting Process

Extraction of the compound B057-250(Cu-, Zn- and Fe-chelates) may be conducted according to a conventional method for extracting fermented products. For example, the culture is extracted with a water-immiscible organic solvent such as ethyl acetate or chloroform, or the filtrate from the culture is adsorbed on synthetic porous high-molecular resin (HP-20) or the like followed by eluting with methanol or acetone, and, after the resultant eluate is concentrated in vacuo, the residue is extracted with an organic solvent such as ethyl acetate.

The resultant crude product can be further purified according to the combination of well-known processes ordinarily used for purification of a liposoluble substance, such as column chromatography using an adsorbent such as silica gel and thin layer chromatography or column chromatography on gel filtration (such as LH-20).

The resultant purified product is precipitated from a variety of mixed solvents to give crystals of compound B057-250. The mixed solvent system includes methanol-water, ethanol-water, methanol-ethyl acetate and the like.

3) Preparation of a Metal Complex of B057-250

B057-250B (Zn-chelate) is substituted with other bivalent or trivalent metal ions to produce a different complex. The bivalent or trivalent metal ions include the same metal ions as those defined in the foregoing M.

The complex can be produced, for example, in the following manner. A solution of a bivalent or trivalent metal salt (such as chloride, sulfate and nitrate) is added to a solution of B057-250B (Zn-chelate) in alcohol (such as methanol or ethanol) which was extracted and isolated from a culture of bacteria such as *Pseudomonas sp.* No.57-250, and after stirring, the mixture is extracted with an organic solvent (such as chloroform and methylene chloride) to give said complex.

The present invention further provides a pharmaceutical composition or a veterinary medicine containing the compound B057-250of the present invention in combination with one or more pharmaceutical acceptable carriers.

The compound B057-250of the present invention is especially useful for prophylaxis or treatment of mycoplasmosis, and therefore, can be used as an anti-mycoplasma agent.

When used as a medicament, the compound can be orally or parenterally administered. For oral administration, the compound of the present invention can be formulated into conventional formulations. For example, any one of a formulation such as a solid formulation such as tablets, powders, granules and capsules; solutions; oil suspensions; or liquid preparations such as syrups or elixirs can be used. For parenteral administration, it can be formulated into aqueous or oil suspensions, or suppositories. Any one of them can be produced using carriers such as commonly used excipients, binders, aqueous and oil solvents, emulsions and suspensions, if necessary, and optionally contains other additives such as preservatives or stabilizing agents.

The compound of the present invention is usually administered at a dose of 50–1000 mg per day which may be divided into 1 to 5 portions, although the dose will vary depending on the administration route, ages, weights and the condition of patients, and the type of diseases.

When used as a veterinary medicine, it can be orally or parenterally administered to domestic fowls and animals such as chickens, swine and cattle. Generally, for oral administration, it is preferably administered in combination with a commonly used carrier (such as defatted rice bran, defatted soy bean meal, wheat bran, kaolin, talc, calcium carbonate, lactic acid and water), or such combination or compound B057-250alone combined with feed for animals or water is preferably administered. The feed for animals may be the ones which are commonly used as feed for animals, such as corn, wheat bran, rice, wheat, cotton seed meal, milo, soy bean meal, fish meal, defatted rice bran, oils and fats, alfalfa, calcium carbonate, calcium phosphate, sodium chloride, choline chloride, vitamins such as vitamin A, vitamin D, vitamin E, vitamin $B_1$, vitamin $B_2$, vitamin $B_6$, vitamin $B_{12}$, calcium pantothenate, nicotinic acid amide and folic acid, and inorganic salts such as magnesium sulfate, ferric sulfate, cupric sulfate, zinc sulfate, potassium iodide and cobalt sulfate. Part or all of them are combined to use.

The contents of the compound B057-250in feed are preferably in the range of 50–200 ppm.

For parenteral administration, it can be used in the same manner as that of the foregoing medicament.

The compound of the present invention is generally administered at a dose of 10–400 mg for oral administration, and 5–200 mg for parenteral administration, per kg of body weights of animal per day. The compound is administered for several consecutive days.

EXAMPLE 1

A. Cultivation

Two or three platinum-loopsful of *Pseudomonas sp.* No. 57-250 from agar plate culture (28° C., 2 days) were inoculated into two 500-mL Sakaguchi flasks each containing 100 mL of seed medium, and then subjected to agitation culture (reciprocating shaker, 200 rpm/min.) at 28° C. for 2 days. 100 mL of the seed culture were subsequently inoculated to two 10-L jar fermentors each containing 5 L of production medium followed by agitation culture at 23° C. for 2 days (agitating at 400 rpm, 5 L of air/min.). The resultant culture was extracted according to the process stated in the following section B.

The media used herein were heart infusion agar for agar plate medium, heart infusion broth for seed culture and 1% glucose, 0.5% yeast extract and 0.3% calcium carbonate for production medium, which were all adjusted to pH 7.0. Seed culture medium and production medium were sterilized at 121° C. for 20 min. and at 121° C. for 1 hour, respectively.

Modified Culture Method

The following example shows a modified method for enhancing the production of compound B (Zn-chelate), which led to about 50 times increase of the production compared with that of the foregoing example.

1) Seed Culture

Bennet medium (1% glucose, 0.2% yeast extract, 0.1% meat extract and 0.2% casamino acid, pH 7) was autoclaved at 121° C. for 20 min. and *Pseudomonas sp.* No. 57-250 was inoculated and cultured at 28° C. using a rotary shaker at 140 rpm for 18 hours.

2) Main Culture

Eighty L of fermentation medium (1% glucose, 2% dextrin, 1% yeast extract, 1% Pharmamedia, 0.0002% cupric sulfate hexahydrate, 0.01% zinc sulfate heptahydrate, pH 6.5) was added to jars (2×50 L, 2×30 L) followed by adding anti-foaming agent (Polypropylene glycol 2000) at a final concentration of 0.01%. After sterilizing at 121° C. for 20 min. and cooling, the seed culture was inoculated at a final concentration of 1%. Then, they were cultured under the following conditions: at 28° C., agitating at 29–600 rpm, aerating at 25 L/min. for 50-L jar and 15 L/min. for 25-L jar, cultured for 42 hours.

B. Extraction and Isolation

1) Extraction and Isolation of Antibiotic B057-250B

To 8.5 L of culture (pH 8.3), an equal amount of ethyl acetate was added and then liquid-liquid partitioning extraction was performed twice. 760 mg of the culture was fractioned by column chromatography (140 g of silica gel, 70–230 mesh, Merck No. 7734. After washing the column with a mixture of dichloromethane/methanol (98:2, v/v), B057-250B was eluted with a mixture of dichloromethane/methanol (95:5, v/v) to give 11 mg of crude product, followed by partitioning to purify using thin layer chromatography (silica gel plate, 20×20 cm, 0.5 mm, Merck No. 5744. After 15-cm developing with a mixture of chloroform/methanol (9:1, v/v), a bright blue band (irradiation with a UV lamp at 365 nm) around an Rf value 0.5 was collected and extracted with a mixture of chloroform/methanol (8:2, v/v) to give B057-250B. Further purification was conducted with a Sephadex LH-20 column (ID 15 mm×870 mm). Thus, the sample was dissolved in a small amount of methanol, followed by isolation with methanol. A fraction (6.6 mg) containing B057-250B was recrystallized from methanol/ethyl acetate to give 3.6 mg of colourless and rhombic board-shaped crystals. m.p.: 226°–228° C. (Decomposition).

2) Extraction and Isolation of Antibiotics B057-250A and C

The titled antibiotics can be prepared according to the process for preparing of B057-250B as described above. 8.5 L of the culture obtained in Section A was extracted with ethyl acetate and then, after silica gel column chromatography, B057-250C and B057-250A were eluted with dichloromethane/methanol (98:2, v/v) and dichloromethane/methanol (9:1, v/v), respectively. Each product was applied to preparative thin layer chromatography and developed with chloroform/methanol (9:1, v/v) by 15 cm. The respective bands containing A and C were found around Rf=0.34 and 0.65 (irradiation with UV lamp), which were collected. The subsequent purification was performed by preparative high-performance liquid chromatography (PREP-HPLC). Column: PREP-ODSM, ID 20 mm×250 ram. Guard column: ID 20 mm×50 mm, Shimadzu Techno Research. Mobile phase: methanol/water (75:25, v/v). Flow rate: 9 mL/min., Detection: UV 235 nm. Temperature: 40° C. Retention time: 21 min. for A, 25 min. for B and 28 min. for C.

According to the above process, 0.4 mg of B057-250A and 1.3 mg of B057-250C were obtained.

3) Extraction and Isolation of Antibiotic B057-250B Produced by the Modified Process About 70 L of the culture were centrifuged and separated into 66 L of the supernatant and the bacterial cells. 3.3 kg of HP-20 was added to the supernatant and agitated at room temperature for 1 hour. HP-20 was filtrated by a mesh filter, washed with water and then filled in a column. After washing with 40 L of deionized water, the column was eluted with methanol to give 12 L of the active fraction. The fraction was concentrated in vacuo and then extracted with ethyl acetate. On the other hand, the bacterial cells were extracted with methanol, and the methanol extract was filtered, concentrated in vacuo and the residue was extracted with ethyl acetate. The ethyl acetate extracts obtained above from the supernatant and the bacterial cells were combined and concentrated to dryness, resulting in 11.3 g of a crude extract.

The crude extract was dissolved in chloroform, charged in a silica gel column (350 g of silica gel, column: 50×350 mm) and then developed with chloroform-methanol. After washing with 500 mL of chloroform and 1.6 L of chloroform-methanol (98:2), the column was eluted with 1.3 L of chloroform-methanol (9:1) to give 5.7 g of a crude fraction containing compound B. Repeated recrystallization of the crude fraction from ethyl acetate-methanol provided 1.73 g of compound B as crystals.

EXAMPLE 2

Preparation of B057-250D (Co-chelate)

50 mg of B057-250B was dissolved in 3 mL of methanol. To the solution were added 1 mL of a 0.5M aqueous solution of cobalt and 15 mL of water, and the resultant solution was mixed with stirring. Subsequently, the mixture was extracted twice with 15 mL of chloroform and the organic layer was concentrated in vacuo to dryness. The residue was recrystallized from ethyl acetate-methanol to give 41.2 mg of the titled compound.
Preparation of the Reagent Used 0.5M Co-solution: 1.2 g of cobaltous chloride. 6H$_2$O was dissolved in 10 mL water.

EXAMPLE 3

Preparation of B057-250E (Ni-chelate)

According to the process as described in the preparation of the Co-chelate, 38.3 mg of the titled compound was obtained.
Preparation of Reagents Used 0.5M Ni-solution: 1.2 g of nickel chloride 6H$_2$O was dissolved in 10 mL water.

EXPERIMENT 1

Antibacterial Spectra of the Compounds in Vitro

For determining the antibacterial activities, Minimum Inhibitory Concentration (MIC, µg/mL) was determined using the agar dilution method designated by the Society for Chemotherapy in Japan, and for Mycoplasma, the liquid dilution method was used for determining MIC. Serpulina and Clostridium, among the bacteria tested were anaerobically cultured using the Gas-pack method. Determination of MIC was conducted using the media having the following compositions depending on the bacteria tested.

PPLO medium (Difco) containing 12% horse serum and 1% glucose was used for Mycoplasma (M.) gallisepticum; Frey medium (Gibco) containing 10% swine serum, 0.01% β-NAD and 1% glucose for M. synoviae; a medium consisting of Hanks solution with 0.5% lactalbumin, 10% horse serum, 5% of a 25% yeast extract, and 1% glucose for M. hyopneumoniae; and PPLO medium (Difco) containing 20% horse serum, 10% of a 25% yeast extract, and 1% glucose for M. pneumoniae. Those media also contained 0.025% phenol red in order to detect the growth of the bacteria according to color changes. MIC values were determined after culturing at 37° C. for 120–168 hours.

Using Mueller Hinton agar (MHA, Difco) containing 5% horse serum for Streptococcus agalactiae and MHA (Difco) containing 0.05% β-NAD for Actinobacillus pleuropneumoniae, those bacteria were cultured at 37° C. for 24–48 hours before determination of MIC. Anaerobic culture was performed using Gas-pack method with Trypticase Soy agar (TSA, BBL) containing 5% defibrinated sheep blood for Serpulina hyodysenteriae and GAM medium (Nissui) for Clostridium perfringens. After culturing Serpulina hyodysenteriae at 37° C. for 96–120 hours and Clostridium perfringens at 37° C. for 24 hours, MICs were determined.

Pasteurella piscicida and Streptococcus. sp. were cultured at 25° C. for 20–24 hours using Brain Heart Infusion agar (BHI, Difco) containing 2% NaCl and Sensitivity-disc N medium (Nissui), respectively, followed by MIC-determination. Other bacteria were cultured at 37° C. for 20–24 hours using MHA for a determination medium before determination of MIC. Table 2 indicates that the compounds have a strong activity specifically against M. gallisepticum, M. synoviae, M. hyopneumoniae and M. pneumoniae.

TABLE 2

MIC (µg/ml) for a variety of bacteria in vitro

| Bacteria tested | MIC (µg/ml) | | | | |
|---|---|---|---|---|---|
| | Zn-chelate | Cu-chelate | Fe-chelate | Co-chelate | Ni-chelate |
| Mycoplasma gallisepticum S6 | 0.1 | 0.1 | 0.2 | 6.25 | 3.13 |
| Mycoplasma gallisepticum field-isolated strain (T)[a] | 0.2 | 0.2 | 0.2 | 12.5 | 6.25 |
| M. pneumoniae Mac | ≤0.00625 | ≤0.00625 | ≤0.00625 | | |
| M. hyopneumoniae ST-11 | 0.025 | 0.05 | 0.1 | | |
| Staphylococcus aureus FDA 209P | 25 | >25 | >25 | | |
| Pasteurella multocida D-6 | 25 | >25 | >25 | | |
| Bordetella bronchiseptica H-16 | 25 | >25 | >25 | | |
| Escherichia coli NIHJ JC-2 | >25 | >25 | >25 | | |
| Salmonella enteritidis 8966(PT34) | >25 | >25 | >25 | | |
| Klebsiella pneumoniae ATCC 27736 | >25 | >25 | >25 | | |
| Streptococcus agalactiae ATCC 9925 | >25 | >25 | >25 | | |
| Actinobacillus pleuro-pneumoniae NB-001(1) | 6.25–12.5 | 3.13 | 12.5 | | |
| Clostridium perfringens ATCC 13124 | 6.25 | 6.25 | 12.5 | | |
| Serpulina hyodysenteriae ATCC 27164 | >25 | 12.5 | >25 | | |
| Pasteurella piscicida No. 2 | >25 | | 25 | | |
| Streptdcoccus sp. SN89119 | >25 | >25 | 25 | | |

[a]Macrolides-resistant strain

EXPERIMENT 2

In Vivo Test Results on Chickens Inoculated with M. gallisepticum

Antibacterial effect of B057-250B on *M. gallisepticum* (MG) field-isolated strain T which is resistant to macrolides was determined at a single dose by forced oral administration.

The test procedure was as follows: 8-day old chickens (male, layer type, 5 chickens/group) were inoculated with $2.3\times10^3$ CFU (colony-forming units) of MG per chicken in their right air sacs, and immediately after inoculation, they received a single dose of 70 mg/kg or 20 mg/kg of B057-250B (dissolved in methanol and then added to 3% gum arabic).

For a control, commercially available chlortetracycline (CTC) and Tylosin (TS) were dissolved in 3% gum arabic for administration. Autopsy of the chickens was performed on the 7th day after infection and the antibacterial effect was determined according to the incidence of the air-sac lesions and severity thereof. The test results are shown in the following Table 3, which indicates that the antibacterial effects of B057-250B are superior to those of commercially available anti-mycoplasma agents.

TABLE 3

Antibacterial effects of the compounds of the invention on chickens inoculated with MG in their air sacs.

| Drugs | Dose | No. of chickens tested | lesions of right air sacs — | Slight | Moderate to severe |
|---|---|---|---|---|---|
| Compound B | 1 × 20 mg/kg | 5 | 0 | 2 | 3 |
| | 1 × 70 mg/kg | 5 | 4 | 1 | 0 |
| CTC | 1 × 50 mg/kg | 5 | 1 | 1 | 3 |
| | 1 × 100 mg/kg | 5 | 2 | 1 | 2 |
| TS | 1 × 100 mg/kg | 5 | 1 | 0 | 4 |
| | 1 × 200 mg/kg | 5 | 0 | 3 | 2 |
| Control infected | | 5 | 0 | 1 | 4 |
| Control not infected | | 5 | 5 | 0 | 0 |

CTC: Chlortetracycline
TS: Tylosin

We claim:

1. A compound of the formula:

wherein M is a bivalent or trivalent metal ion and X is OH or $O^{\ominus}$.

2. The compound of claim 1 of the formula:

wherein M and X are as defined in claim 1.

3. A compound of claim 2 wherein M is $Zn^{2+}$, $Cu^{2+}$, $Fe^{2+}$, $Fe^{3+}$, $Co^{2+}$, $Ni^{2+}$, $Mn^{2+}$, $Mn^{3+}$, $Cd^{2+}$, $Mg^{2+}$, $Ca^{2+}$, $Sr^{2+}$, $Ba^{2+}$, $V^{2+}$, $V^{3+}$, $Cr^{2+}$, $Al^{3+}$, $Sn^{2+}$, $Pb^{2+}$ or $Ag^{2+}$.

4. A compound of claim 2 wherein M is $Zn^{2+}$, $Cu^{2+}$, $Fe^{3+}$, $Co^{2+}$ or $Ni^{2+}$.

5. The compound of claim 1 wherein M is $Zn^{2+}$, $Cu^{2+}$, $Fe^{2+}$, $Fe^{3+}$, $Co^{2+}$, $Ni^{2+}$, $Mn^{2+}$, $Mn^{3+}$, $Cd^{2+}$, $Mg^{2+}$, $Ca^{2+}$, $Sr^{2+}$, $Ba^{2+}$, $V^{2+}$, $V^{3+}$, $Cr^{2+}$, $Al^{3+}$, $Sn^{2+}$, $Pb^{2+}$ or $Ag^{2+}$.

6. The compound of claim 1 wherein M is $Zn^{2+}$, $Cu^{2+}$, $Fe^{3+}$, $Co^2$+ or $Ni^{2+}$.

7. A pharmaceutical composition containing the compound of claim 1 in combination with one or more pharmaceutically acceptable carriers.

8. A veterinary composition containing the compound of claim 1 in combination with one or more pharmaceutically acceptable carriers.

9. An anti-mycoplasma agent containing the compound of claim 1 in combination with one or more pharmaceutically acceptable carriers.

10. A process for preparing a compound of the formula:

where M° is $Cu^{2+}$, $Zn^{2+}$ or $Fe^{3+}$ and X is OH or $O^{\ominus}$, which comprises culturing *Pseudomonas sp.* No. 57-250, FERM BP-5143, in an aqueous nutrient medium containing assimilable sources of carbon, nitrogen and inorganic substances, and extracting and collecting said compound from the culture.

11. A process for replacing the metal ion M° in the compound of claim 10, comprising reacting a solution of said compound with a solution containing a divalent or trivalent metal ion M to obtain a compound containing said metal ion M.

* * * * *